US00PP20655P2

(12) United States Plant Patent
Michalik

(10) Patent No.: US PP20,655 P2
(45) Date of Patent: Jan. 19, 2010

(54) *GERANIUM* PLANT NAMED 'REGLI'

(50) Latin Name: *Pelargonium grandiflorum*
Varietal Denomination: Regli

(75) Inventor: Andrea Michalik, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 367 days.

(21) Appl. No.: 11/820,029

(22) Filed: Jun. 15, 2007

(51) Int. Cl.
*A01H 5/00* (2006.01)

(52) U.S. Cl. ..... Plt./331

(58) Field of Classification Search ..... Plt./331
See application file for complete search history.

*Primary Examiner*—Kent L Bell
(74) *Attorney, Agent, or Firm*—C. A. Whealy

(57) ABSTRACT

A new and distinct cultivar of Regal *Geranium* plant named 'Regli', characterized by its upright and mounded plant habit; vigorous growth habit; freely basal branching habit; early and freely flowering habit; large pink and purple-colored flowers; and no requirement for cooling treatment for flower development.

1 Drawing Sheet

Botanical designation: *Pelargonium grandiflorum.*
Cultivar denomination: 'Regli'.

BACKGROUND OF THE INVENTION

The present invention relates to a new and distinct cultivar of Regal *Geranium*, botanically known as *Pelargonium grandiflorum*, and hereinafter referred to by the name 'Regli'.

The new Regal *Geranium* is a product of a planned breeding program conducted by the Inventor in Dresden, Germany. The objective of the breeding program is to develop new Regal *Geraniums* that do not require a cooling treatment for flower development.

The new Regal *Geranium* is a naturally-occurring branch mutation of the *Pelargonium grandiflorum* cultivar Regros, not patented. The cultivar Regli was discovered and selected by the Inventor on a single plant of the parent cultivar in a controlled environment in Dresden, Germany during the summer of 2003.

Asexual reproduction of the new Regal *Geranium* by vegetative terminal cuttings in a controlled environment in Dresden, Germany since the summer of 2003, has shown that the unique features of this new Regal *Geranium* are stable and reproduced true to type in successive generations.

SUMMARY OF THE INVENTION

The cultivar Regli has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Regli'. These characteristics in combination distinguish 'Regli' as a new and distinct cultivar of Regal *Geranium*:

1. Upright and mounded plant habit.
2. Vigorous growth habit.
3. Freely basal branching habit.
4. Early and freely flowering habit.
5. Large pink and purple-colored flowers.
6. Does not require cooling treatment for flower development.

Plants of the new Regal *Geranium* differ primarily from plants of the parent, the cultivar Regros, primarily in flower color as plants of the cultivar Regros have light red-colored flowers.

Plants of the new Regal *Geranium* can be compared to plants of the *Pelargonium grandiflorum* cultivar Pacali, disclosed in U.S. Plant Pat. No. 16,755. In side-by-side comparisons conducted in Dresden, Germany, plants of the new Regal *Geranium* differed from plants of the cultivar Pacali in the following characteristics:

1. Plants of the new Regal *Geranium* were broader than plants of the cultivar Pacali.
2. Plants of the new Regal *Geranium* had shorter internodes than plants of the cultivar Pacali.
3. Plants of the new Regal *Geranium* had larger flower umbels with more flowers per umbel than plants of the cultivar Pacali.
4. Plants of the new Regal *Geranium* and the cultivar Pacali differed in flower color.
5. Plants of the new Regal *Geranium* had longer peduncles than plants of the cultivar Pacali.

BRIEF DESCRIPTION OF THE PHOTOGRAPH

The accompanying colored photograph illustrates the overall appearance of the new Regal *Geranium*, showing the colors as true as it is reasonably possible to obtain in colored reproductions of this type. Colors in the photograph may differ slightly from the color values cited in the detailed botanical description which accurately describe the colors of the new Regal *Geranium*. The photograph comprises a side perspective view of a typical flowering plant of 'Regli' grown in a container.

DETAILED BOTANICAL DESCRIPTION

The aforementio ned photograph and following observations, measurements and values describe plants grown in Dresden, Germany in a glass-covered greenhouse during the winter and spring and under conditions which closely approximate commercial *Geranium* production. During the production of the plants, day temperatures averaged 18° C., night temperatures averaged 16° C. and light levels ranged from 15 kilolux to 100 kilolux. Plants were about six months old when the photograph and the description were taken. In the detailed description, color references are made to The Royal Horticultural Society Colour Chart, 1995 Edition, except where general terms of ordinary dictionary significance are used.

Botanical classification: *Pelargonium grandiflorum* cultivar Regli.

Parentage: Naturally-occurring branch mutation of the *Pelargonium grandiflorum* cultivar Regros, not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 20° C.

*Time to produce a rooted young plant, summer.*—About 25 days at temperatures of 20° C.

*Time to produce a rooted young plant, winter.*—About 30 days at temperatures of 20° C.

*Root description.*—Fine, fibrous; white in color.

*Rooting habit.*—Freely branching; dense.

Plant description:

*Plant/growth habit.*—Upright and mounded plant habit; inverted triangle; densely foliated. Vigorous growth habit. Freely basal branching habit with about seven lateral branches developing per plant.

*Plant height, to top of umbels.*—About 28 cm.

*Plant height, to top of leaves.*—About 17 cm.

*Plant width.*—About 40 cm.

*Lateral branches.*—Length: About 10 cm. Diameter: About 6 mm. Internode length: Less than 1 cm. Texture: Pubescent. Color: 138A.

Foliage description:

*Arrangement.*—Alternate or opposite; simple. Length: About 6 cm. Width: About 8 cm. Shape: Roughly cordate; palmately lobed. Apex: Acute. Base: Cordate, open. Margin: Serrate to biserrate.

*Venation pattern.*—Palmate.

*Texture, upper and lower surfaces.*—Sparsely pubescent; leathery.

*Color.*—Developing and fully expanded foliage, upper surface: 137B; venation, 144A. Developing and fully expanded foliage, lower surface: 147B; venation, 144A. Zonation pattern: Not discernible. Petiole: Length: About 5 cm. Diameter: About 4 mm. Texture, upper and lower surfaces: Pubescent. Color, upper and lower surfaces: 144A.

Flower description:

*Flower arrangement.*—Single rotate flowers arranged in inversely conical umbels arising from apical leaf axils. Umbels displayed above the foliage on strong peduncles. Flowers face upright to outward. Flowers not persistent. Flowers not fragrant.

*Quantity of flowers.*—Freely flowering habit; about 30 flower umbels per plant each with about seven flowers.

*Flowering season.*—In Dresden, Germany, flowering initiates in the spring and continues into the summer. Plants do not require a cooling treatment for flower development.

*Flower longevity.*—Individual flowers last about two weeks on the plant.

*Umbel height.*—About 6 cm.

*Umbel diameter.*—About 8 cm.

*Flower diameter.*—About 5 cm.

*Flower depth* (*height*).—About 3 cm.

*Flower buds.*—Length: About 2 cm. Diameter: About 1 cm. Shape: Roughly elliptical. Color: 146B.

*Petals.*—Quantity per flower: Five; imbricate. Length: About 3.5 cm. Width: Upper two petals, about 3 cm. Lower three petals, about 2.5 cm. Shape: Obovate. Apex: Rounded. Base: Cuneate. Margin: Entire. Texture, upper and lower s urfaces: Smooth, glabrous; satiny. Color: When opening and fully opened, upper surface: 74D; upper petals, towards the center, 74A to darker than 74A, central spot, close to 59A; venation, 74A. When opening and fully opened, lower surface: 75C; venation, 74B.

*Sepals.*—Quantity per flower: Five, arranged in a single whorl. Length: About 1.5 cm. Width: About 5 mm. Shape: Lanceolate. Apex: Acute. Margin: Entire. Texture, upper and lower surfaces: Pubescent. Color, upper and lower surfaces: 143A.

*Peduncle* (*umbel stem*).—Length: About 5 cm. Diameter: About 3 mm. Strength: Strong. Angle: Mostly erect to outwardly slanted. Texture: Pubescent. Color: 146B.

*Pedicel* (*individual flower stem*).—Length: About 2 cm. Diameter: About 2 mm. Strength: Strong; flexible. Texture: Pubescent. Color: 146B.

*Reproductive organs.*—Androecium: Stamen quantity per flower: About seven. Anther length: About 2 mm. Anther shape: Tubular. Anther color: 72A. Pollen amount: Abundant. Pollen color: 171A. Gynoecium: Pistil quantity per flower: One. Pistil length: About 2 cm. Stigma shape: Five-parted. Stigma color: Darker than 59A. Style length: About 4 mm. Style color: Darker than 59A. Ovary color: Close to 146C.

*Seeds.*—Length: About 2 mm to 3 mm. Diameter: About 1 mm. Color: Brownish.

Disease/pest resistance: Plants of the new Regal *Geranium* have not been observed to be resistant to pathogens and pests common to Regal *Geraniums*.

Temperature tolerance: Plants ofthe new Regal *Geranium* have been observed to tolerate temperatures ranging from about 1° C. to about 35° C. to 40° C.

It is claimed:

1. A new and distinct Regal *Geranium* plant named 'Regli' as illustrated and described.

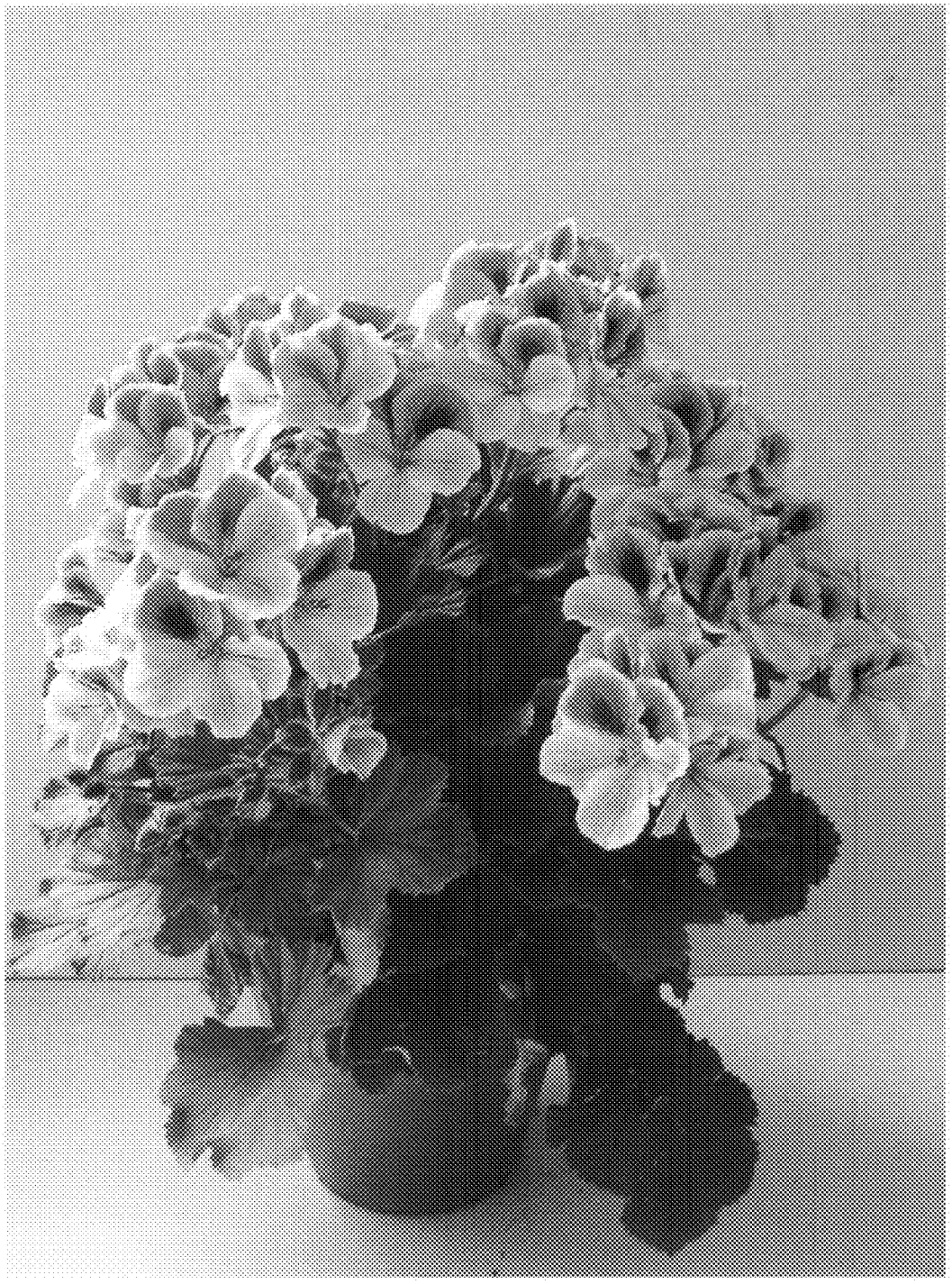

* * * * *